(12) United States Patent
Fischell et al.

(10) Patent No.: US 8,591,495 B2
(45) Date of Patent: *Nov. 26, 2013

(54) INTRODUCER SHEATH WITH THIN-WALLED SHAFT

(75) Inventors: Robert E. Fischell, Dayton, MD (US);
Tim A. Fischell, Kalamazoo, MI (US);
David R. Fischell, Fairhaven, NJ (US)

(73) Assignee: Fischell Innovations, LLC, Dayton, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/431,526

(22) Filed: Mar. 27, 2012

(65) Prior Publication Data

US 2013/0079746 A1    Mar. 28, 2013

Related U.S. Application Data

(63) Continuation-in-part of application No. 13/032,876, filed on Feb. 23, 2011, now Pat. No. 8,348,925.

(51) Int. Cl.
*A61M 25/00* (2006.01)

(52) U.S. Cl.
USPC ............................................. 604/526

(58) Field of Classification Search
USPC .................................. 604/523–532
See application file for complete search history.

(56) References Cited

U.S. PATENT DOCUMENTS

| | | |
|---|---|---|
| 4,224,937 A | 9/1980 | Gordon |
| 4,362,156 A | 12/1982 | Feller, Jr. et al. |
| 4,705,511 A | 11/1987 | Kocak |
| 4,862,891 A | 9/1989 | Smith |
| 4,976,689 A | 12/1990 | Buchbinder et al. |
| 4,997,421 A | 3/1991 | Palsrok et al. |
| 5,069,674 A | 12/1991 | Fearnot et al. |
| 5,180,376 A | 1/1993 | Fischell |
| 5,324,262 A | 6/1994 | Fischell et al. |
| 5,360,432 A | 11/1994 | Shturman |
| 5,413,562 A | 5/1995 | Swauger |
| 5,423,774 A | 6/1995 | Fischell et al. |
| 5,454,795 A * | 10/1995 | Samson ................. 604/526 |
| 5,484,425 A | 1/1996 | Fischell et al. |
| 5,496,344 A | 3/1996 | Kanesaka et al. |
| 5,514,236 A | 5/1996 | Avellanet et al. |
| 5,531,721 A | 7/1996 | Pepin et al. |
| 5,630,806 A | 5/1997 | Inagaki et al. |

(Continued)

FOREIGN PATENT DOCUMENTS

WO    WO2009045276    4/2009

OTHER PUBLICATIONS

International Search Report and Written Opinion dated Nov. 8, 2012 for PCT/US2012/40391.

(Continued)

*Primary Examiner* — Kevin C Sirmons
*Assistant Examiner* — Andrew Gilbert
(74) *Attorney, Agent, or Firm* — Stoel Rives LLP

(57) ABSTRACT

A thin-walled introducer sheath is described. In some embodiments, the introducer sheath includes structural support components, such as wires, used in connection with a polymeric inner coating, a polymeric outer coating, or both. Further, in some embodiments, the wire components are annealed to reduce cold-work-related stresses and hardness. Use of annealed components may enable a reduction in the thickness of the polymeric outer coating in some applications.

20 Claims, 8 Drawing Sheets

(56) References Cited

U.S. PATENT DOCUMENTS

| | | | |
|---|---|---|---|
| 5,658,264 A * | 8/1997 | Samson | 604/526 |
| 5,700,253 A | 12/1997 | Parker | |
| 5,702,373 A * | 12/1997 | Samson | 604/527 |
| 5,704,926 A | 1/1998 | Sutton | |
| 5,796,044 A | 8/1998 | Cobian et al. | |
| 5,827,230 A | 10/1998 | Bierman | |
| 5,827,239 A | 10/1998 | Dillon et al. | |
| 5,863,366 A | 1/1999 | Snow | |
| 5,879,499 A | 3/1999 | Corvi | |
| 5,891,114 A * | 4/1999 | Chien et al. | 604/527 |
| 5,927,345 A | 7/1999 | Samson | |
| 5,944,697 A | 8/1999 | Biche | |
| 5,947,940 A * | 9/1999 | Beisel | 604/526 |
| 5,976,120 A | 11/1999 | Chow et al. | |
| 6,152,912 A * | 11/2000 | Jansen et al. | 604/526 |
| 6,165,163 A * | 12/2000 | Chien et al. | 604/523 |
| 6,264,684 B1 * | 7/2001 | Banas et al. | 623/1.13 |
| 6,338,725 B1 | 1/2002 | Hermann et al. | |
| 6,533,770 B1 | 3/2003 | Lepulu et al. | |
| 6,863,674 B2 | 3/2005 | Kasahara et al. | |
| 6,939,337 B2 | 9/2005 | Parker et al. | |
| 6,945,956 B2 * | 9/2005 | Waldhauser et al. | 604/95.01 |
| 7,083,588 B1 | 8/2006 | Schmulewitz et al. | |
| 7,112,298 B2 * | 9/2006 | Kampa et al. | 264/301 |
| 7,320,697 B2 | 1/2008 | Demond et al. | |
| 7,331,966 B2 | 2/2008 | Soma et al. | |
| 7,438,712 B2 | 10/2008 | Chouinard | |
| 7,618,430 B2 | 11/2009 | Scheib | |
| 7,655,021 B2 | 2/2010 | Brasington et al. | |
| 7,815,762 B2 | 10/2010 | Lentz et al. | |
| 7,905,877 B1 * | 3/2011 | Jimenez et al. | 604/525 |
| 8,034,045 B1 | 10/2011 | Lyons | |
| 8,262,625 B1 | 9/2012 | Fischell et al. | |
| 8,348,925 B2 * | 1/2013 | Fischell et al. | 604/526 |
| 2001/0010247 A1 | 8/2001 | Snow | |
| 2001/0044633 A1 * | 11/2001 | Klint | 606/200 |
| 2002/0169377 A1 | 11/2002 | Khairkhanan et al. | |
| 2003/0093060 A1 * | 5/2003 | Kempf | 604/527 |
| 2003/0225365 A1 | 12/2003 | Greff et al. | |
| 2003/0229313 A1 | 12/2003 | Bierman | |
| 2004/0010243 A1 | 1/2004 | Klint | |
| 2004/0068249 A1 * | 4/2004 | Kampa et al. | 604/523 |
| 2004/0116960 A1 | 6/2004 | Demond et al. | |
| 2004/0153049 A1 | 8/2004 | Hewitt et al. | |
| 2004/0236346 A1 * | 11/2004 | Parker | 606/108 |
| 2005/0021022 A1 | 1/2005 | Sturm et al. | |
| 2005/0060017 A1 * | 3/2005 | Fischell et al. | 623/1.11 |
| 2005/0149060 A1 | 7/2005 | Thorstenson et al. | |
| 2005/0228479 A1 | 10/2005 | Pavcnik et al. | |
| 2006/0064054 A1 | 3/2006 | Sakakine et al. | |
| 2006/0089618 A1 | 4/2006 | McFerran et al. | |
| 2006/0095050 A1 | 5/2006 | Hartley et al. | |
| 2006/0155302 A1 * | 7/2006 | Sisken et al. | 606/108 |
| 2007/0066958 A1 | 3/2007 | Wright | |
| 2007/0118207 A1 | 5/2007 | Amplatz et al. | |
| 2007/0185521 A1 | 8/2007 | Bue et al. | |
| 2007/0219500 A1 | 9/2007 | Wright et al. | |
| 2008/0051758 A1 | 2/2008 | Rioux et al. | |
| 2008/0097516 A1 | 4/2008 | Chang et al. | |
| 2008/0243081 A1 * | 10/2008 | Nance et al. | 604/164.03 |
| 2009/0018525 A1 | 1/2009 | Waite et al. | |
| 2009/0054845 A1 | 2/2009 | Puhasmagi et al. | |
| 2009/0157162 A1 * | 6/2009 | Chow et al. | 623/1.11 |
| 2009/0234295 A1 | 9/2009 | Lampropoulos et al. | |
| 2009/0240202 A1 | 9/2009 | Drasler et al. | |
| 2009/0287182 A1 * | 11/2009 | Bishop et al. | 604/509 |
| 2009/0306591 A1 | 12/2009 | Amisar et al. | |
| 2009/0306603 A1 | 12/2009 | Bierman et al. | |
| 2010/0016837 A1 | 1/2010 | Howat | |
| 2010/0049168 A1 | 2/2010 | Parker et al. | |
| 2011/0160702 A1 | 6/2011 | Jimenez et al. | |
| 2011/0245775 A1 | 10/2011 | Tekulve | |
| 2012/0215174 A1 | 8/2012 | Fischell et al. | |
| 2012/0265282 A1 | 10/2012 | Fischell et al. | |
| 2012/0310212 A1 * | 12/2012 | Fischell et al. | 604/523 |

OTHER PUBLICATIONS

International Search Report and Written Opinion dated Sep. 24, 2012 for PCT/US2012/043243.
Restriction Requirement dated Nov. 18, 2011 for U.S. Appl. No. 13/032,876.
Office Action dated Dec. 8, 2011 for U.S. Appl. No. 13/032,876.
Office Action dated Mar. 1, 2012 for U.S. Appl. No. 13/032,876.
Office Action dated May 25, 2012 for U.S. Appl. No. 13/032,876.
Office Action dated Sep. 21, 2012 for U.S. Appl. No. 13/150,308.
International Search Report and Written Opinion dated Aug. 7, 2012 for PCT/US2012/035268.
Notice of Allowance dated Oct. 16, 2012 for U.S. Appl. No. 13/032,876.
Office Action dated Jun. 3, 2013 for U.S. Appl. No. 13/349,060.
Office Action dated Feb. 21, 2013 for U.S. Appl. No. 13/150,308.
Office Action dated Mar. 19, 2013 for U.S. Appl. No. 13/085,951.
International Search Report and Written Opinion dated Apr. 25, 2013 for PCT/US2013/020941.
Notice of Allowance dated Jul. 9, 2013 for U.S. Appl. No. 13/150,308.
International Search Report and Written Opinion dated Jul. 18, 2013 for PCT/US2013/033840.

\* cited by examiner

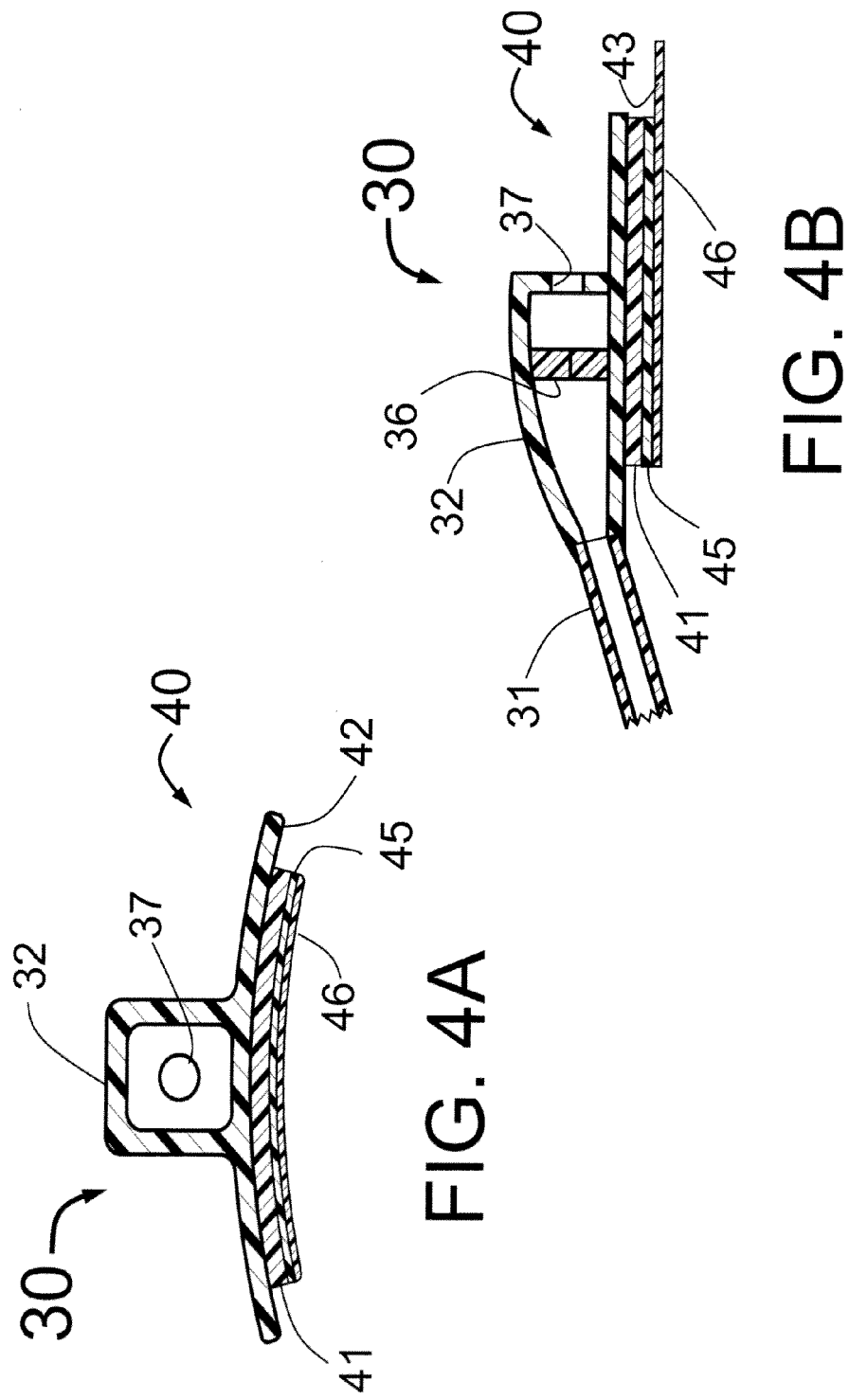

INTRODUCER SHEATH WITH THIN-WALLED SHAFT

RELATED APPLICATIONS

This application is a continuation-in-part of U.S. patent application Ser. No. 13/032,876, filed on Feb. 23, 2011, titled: INTRODUCER SHEATH WITH THIN-WALLED SHAFT AND IMPROVED MEANS FOR ATTACHMENT TO THE SKIN, which issued as U.S. Pat. No. 8,348,925, on Jan. 8, 2013, which is herein incorporated by reference.

FIELD OF USE

This invention is in the field of devices to assist in the placement of catheters through the skin to treat certain coronary and peripheral vascular disorders.

BRIEF DESCRIPTION OF THE DRAWINGS

FIG. 4A is a cross section at "A-A" of FIG. 3 showing the construction of the adhesive pad and the hemostasis valve.

FIG. 4B is a cross section at "B-B" of FIG. 3 showing the construction of the adhesive pad and the hemostasis valve.

DETAILED DESCRIPTION

Figure 1:
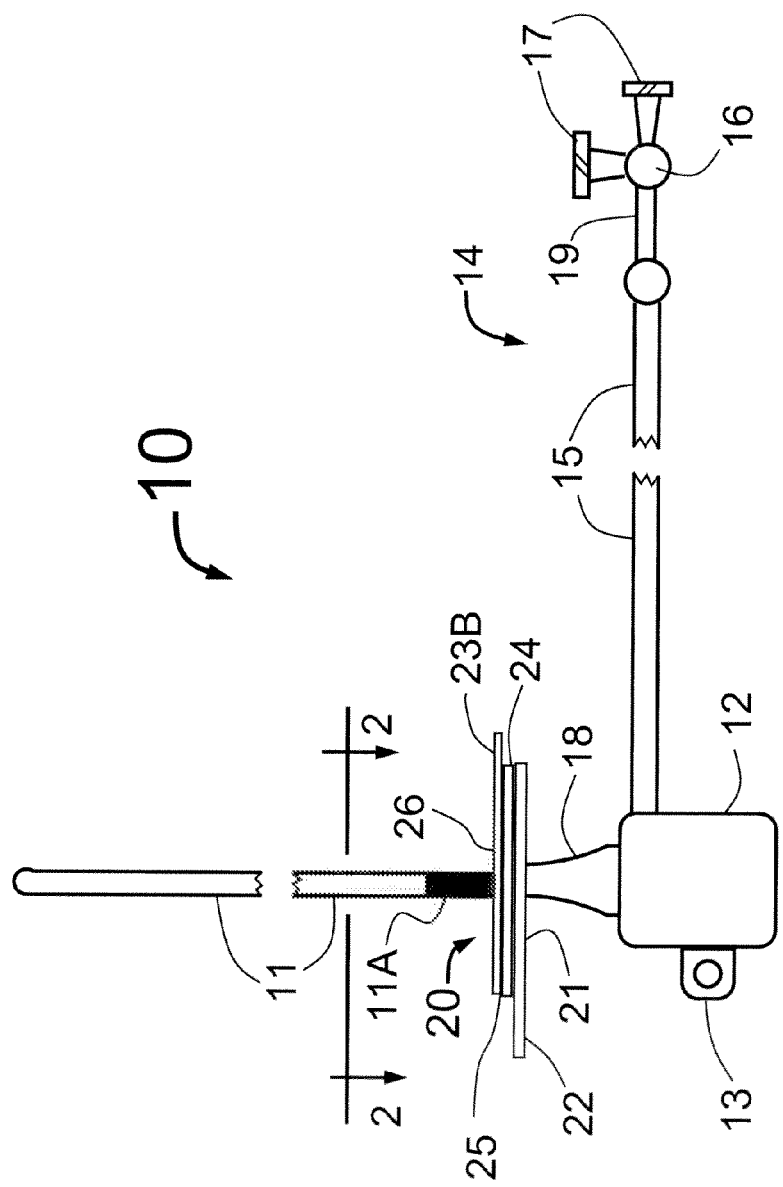
FIG. 1 is a top view of an introducer sheath having a pressure sensitive adhesive pad located at the distal end of the strain relief that is attached to the proximal end of the introducer sheath shaft.

At the present time, physicians place an introducer sheath through the skin of a patient to access that patient's vascular system. Two usual places to gain access are through the skin at the groin to enter the femoral artery and through the skin in the wrist to access the radial artery. After the introducer sheath is placed through the skin, the physician will typically use a suture to fasten the proximal end of the introducer sheath to the patient's skin. That process requires the opening of an additional package that contains the suture thread and a needle and also requires skin penetration that can be somewhat painful for the patient and has the possibility of infection.

Another problem experienced by physicians who insert vascular sheaths is the considerable force that is required to pull a guiding catheter out of an introducer sheath. Thus, any means that can reduce the frictional force experienced in pulling a guiding catheter out of the introducer sheath would be an improvement that would be appreciated by operators who perform this procedure.

Another problem with current sheaths is vascular access bleeding that sometimes occurs after the sheath has been removed. In general, there is a relationship between the outer diameter of the inserted sheath and the risk of bleeding complications. Thus, sheaths with thinner walls would decrease the size of the hole at the vascular entry site and doing that would reduce bleeding complications.

Still another problem experienced by physicians who insert vascular sheaths is the complication of accidental sheath withdrawal from the vascular entry site during the procedure. particularly when a catheter is withdrawn from the sheath. This complication can be minimized by adhesively attaching the proximal end of the sheath to the skin with an adhesive as described herein. Also, making the proximal portion of the shaft of the sheath (portion in the subcutaneous tissue) less lubricious. And by decreasing the frictional force exerted on the sheath's hemostasis valve during catheter removal decrease the propensity for the sheath to be inadvertently pulled out of the blood vessel.

One feature of some embodiments of the present disclosure is a novel attachment means located near the proximal end of the sheath. This attachment means is designed to facilitate rapid attachment and detachment of the proximal end of the sheath to the patient's skin. One embodiment of the present disclosure is an introducer sheath that is improved by having an adhesive pad located at or near the sheath's proximal end that detachably attaches the introducer sheath to the patient's skin without requiring any additional parts that come from a separate sterile package such as a needle and a suture. Specifically, one embodiment of the present disclosure is an adhesive pad located at the distal end of the strain relief section of the shaft of the introducer sheath in close proximity to the hemostasis valve that is located at the proximal end of the introducer sheath. The adhesive pad has a pressure sensitive adhesive on one side that is covered by a removable plastic cover sheet which is removed to expose the pressure sensitive adhesive surface of the adhesive pad in order to attach the introducer sheath to the skin. Either before or after the shaft of the introducer sheath is placed through the skin, the thin plastic (or paper) cover sheet that covers the pressure sensitive adhesive is removed. When the introducer sheath is then advanced into the target blood vessel to its fully inserted position, and the plastic cover sheet of the adhesive pad has been removed, the pressure sensitive adhesive pad is then pushed firmly against the skin thereby firmly attaching the sheath to the patient's skin without requiring a sutured connection.

One aspect of some embodiments of the present disclosure is an adhesive pad that can be placed at a location that is in close proximity to the hemostasis valve located at the proximal end of the introducer sheath. In one embodiment, the adhesive pad is retained at the distal end of the strain relief where it is joined to the proximal end of the shaft of the introducer sheath. If there is no strain relief, then the adhesive pad can be attached to the distal end of the hemostasis valve which is pushed against the skin when the introducer sheath is fully inserted into the patient's vascular system.

In another embodiment, an adhesive pad is attached to the bottom surface of the hemostasis valve. The adhesive pad is joined to the bottom surface of the hemostasis valve through a spongy material that allows the pressure sensitive adhesive to more readily cover any skin surface even if it is somewhat irregular. Still another embodiment utilizes a pressure sensitive adhesive pad that is attached to the hemostasis valve and also wrapped around the patient's wrist. This design would be particularly applicable for the placement of the introducer sheath into the radial artery in the arm.

Another embodiment of the present disclosure is a diaphragm for the hemostasis valve that has a lubricity coating so as to minimize the frictional force that occurs when a catheter is either advanced or pulled back through the diaphragm of the hemostasis valve. This feature allows a catheter to be inserted into or removed from the patient's blood vessel with less resistance thus reducing the tendency to pull the introducer sheath out of that blood vessel during catheter removal. This can be combined with another novel feature using a differential of lubricity coating on the outer surface of the sheath such that a proximal portion of the sheath (portion residing in the subcutaneous tissue) would not have a lubricious (e.g., hydrophilic) coating but the more distal aspect of the outer surface of the sheath's shaft would have a lubricious coating for easy insertion through the patient's skin. This lack of lubricity coating along a proximal portion of the shaft of the sheath will tend to create some resistance to accidental sheath removal from its vascular entry site during catheter removal from the sheath.

The use of a suture is now the only means that is used to make the attachment of the proximal end of an introducer sheath to the skin. The present disclosure eliminates the extra time required to open a separate package containing the needle and suture material, and the time required to place the suture through the introducer sheath and into the skin. The present disclosure eliminates the penetration of the skin that can be somewhat uncomfortable for the patient and increases the possibility of infection. Still further, the cost of the needle and suture in a sterile pack is avoided. It is believed that suturing for retention of the sheath will require about 2 minutes of time for the operator. As a comparison, removing a plastic sheet cover from a pressure sensitive adhesive attachment to the sheath's proximal end and pushing the pressure sensitive adhesive against the skin could probably be done in only 2 seconds. Furthermore, removing the suture could again take about 2 minutes where removing the pressure sensitive adhesive pad would probably take less than 2 seconds. Such time saving and ease of use is appreciated by those physicians who perform this procedure.

Another aspect of the present disclosure is the construction of the tubular shaft of the introducer sheath. Existing introducer sheaths have a wall thickness that is typically greater than 13 mils where 1.0 mil=0.001 inch. By using a flat wire helical coil with a wire thickness of approximately 1 mil to 3 mils, which coil has a very thin coating of plastic placed onto its inner and outer surfaces, it is possible to reduce the wall thickness of the tubular shaft to less than 7 mils and preferably around 5 mils. Such a novel construction would reduce the outside diameter of the introducer sheath by approximately one French size compared to existing introducer sheaths. The diameter of a catheter expressed in French when divided by three gives the diameter of the shaft in millimeters. Such a reduction in the diameter of the sheath would be highly advantageous in reducing the risk of bleeding at the groin that sometimes occurs after removal of sheaths having a larger outside diameter. Any method to decrease the requirement for surgical repair and or a blood transfusion often needed for a major bleeding complication would be highly advantageous for the patient and would significantly decrease the morbidity, mortality and cost associated with catherization procedures. The present disclosure also envisions that the shaft of the sheath would employ a thin-walled, flat wire helical coil to be fabricated from a shape memory alloy such as Nitinol to prevent the possibility of kinking of the tubular shaft of the introducer sheath. Still further the present disclosure envisions a shaft made from two to four separate helical metal coils, one of a cobalt chromium alloy (e.g.; L605) to enhance the strength and radiopacity of the shaft and the other coil(s) to be made from stainless steel for cost economy. This novel design would be very advantageous for providing a thin-walled shaft for the sheath that is also radiopaque and reasonably economical to build. It is also envisioned that just using cobalt chromium alloy flat wires wound two at a time onto an inner Teflon layer and then coated in plastic could be an excellent design.

Still another embodiment of the presently disclosed sheath includes an attachment component with a helical round wire having a sharpened distal end. The helical wire, which is in the form of a corkscrew, would have a handle that can be used to rotate the helical wire so that it can attach the proximal end of the sheath to the skin. This would provide an alternate means to attach and detach the sheath from the skin without the need for a separate suture.

Thus one object of the present disclosure is to provide a means to secure the proximal end of an introducer sheath to a patient's skin without the use of a suture, this means being integrated into the proximal region of the introducer sheath.

Another object of the present disclosure is to secure the proximal end of an introducer sheath to a patient's skin by means of a pressure sensitive adhesive pad without the use of a suture.

Still another object of this disclosure is to secure the proximal end of an introducer sheath to the skin without using a needle and suture so as to eliminate the discomfort that may be felt by the patient when a needle is used to penetrate his or her skin.

Still another object of this disclosure is to attach the proximal end of an introducer sheath to the patient's skin using a pressure sensitive adhesive pad attached to the hemostasis valve thereby eliminating the possibility of an infection where suture material penetrates the patient's skin.

Still another object of this disclosure is to place a lubricious coating on most of the outer surface of the shaft of the introducer sheath that passes through the patient's skin except for a comparatively short region that is in close proximity to the hemostasis valve at the proximal end of the introducer sheath.

Still another object of this disclosure is to have a shaft for the introducer sheath that has an outside diameter that is at least one French size smaller than commercially available introducer sheaths having the same inside diameter, so as to minimize bleeding complications at the vascular entry site.

Still another object of this disclosure is to have a shaft for the introducer sheath that uses at least two separate, thin-walled, flat wire, helical structures made from at least two different metals, this thin-walled structure having plastic materials on its inside and outside surfaces.

Still another object of this disclosure is to have a shaft for the introducer sheath that uses a thin-walled, flat wire, helical structure made from a shape memory alloy such as Nitinol so as to prevent kinking of the thin-walled sheath when it is inserted in the patient's vascular system, the thin-walled structure having plastic materials on its inside and outside surfaces.

Still another object of this disclosure is to have a method for reducing the need for a blood transfusion after an interventional procedure using an introducer sheath by reducing the outside diameter of the tubular shaft that passes through the patient's skin to access the patient's vascular system.

Still another object of this disclosure is to decrease the frictional force that is required as a guiding catheter is either advanced forward or pulled out of the introducer sheath by the use of a lubricity agent placed onto the diaphragm of the hemostasis valve.

Yet another object of the present disclosure is to have a helical wire with a handle that is attached to the proximal end of the sheath where the wire is advanced like a corkscrew to attach and detach the proximal end of the sheath to the patient's skin to reduce the time otherwise needed to get and attach a separate suture.

Again, catheters, sheaths, dilators, guidewires, and other treatment devices are often used in connection with minimally invasive treatments and therapies, such as minimally invasive therapies within the human vasculature. The disclosure below refers specifically to the placement and use of such devices to access and treat disorders within the vasculature. Notwithstanding any specific examples and references, the current disclosure is applicable to any treatment involving placement of elongated devices within body lumens.

As part of some treatment procedures, a physician inserts an introducer sheath through the skin of a patient to access the patient's vascular system. For example, a physician may place an introducer sheath through the skin to access the femoral artery at the groin or the radial artery at the wrist. In some instances, such sheaths are configured with small diameters to reduce the risk of bleeding and other complications once the sheath is removed following therapy. Because the inside diameter of a sheath is dictated, in some procedures, by the size of the instruments to be passed through that sheath, in some instances the outside diameter of a sheath can be decreased by minimizing the wall thickness of the sheath.

Thin-walled sheaths, however, may be prone to kinking and other deformation that prevents or hinders use of the sheath in therapy. In some instances a metal scaffolding structure, for example, a helical wire structure, can be integrated within the wall of the sheath to prevent kinking of the sheath.

In some embodiments, scaffolding reinforced sheathes include heat-treated scaffolding structures to further minimize wall thickness and reduce kinking. In some embodiments, the scaffolding structure provides resistance to kinking, while heat treating the scaffolding structure reduces the tendency of the structure to deform, thus requiring a minimal amount of plastic in the wall to retain the scaffolding. Furthermore, in some embodiments the tip of the sheath is also formed with the plastic components of the sheath wall.

It will be readily understood that the components of the embodiments, as generally described and illustrated in the figures herein, could be arranged and designed in a variety of configurations. Thus, the following more detailed description of one embodiment, as represented in the figures, is not intended to limit the scope of the disclosure, but is merely representative of one of several various embodiments. While the various aspects of the embodiments are presented in the drawings, the drawings are not necessarily drawn to scale.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest to a practitioner while the practitioner is using or manipulating the device, while the distal end is the opposite end. For example, the proximal end of a catheter or sheath used in minimally invasive vascular treatment is the end accessible to a practitioner during use, while the distal end is disposed within a patient's vascular system when the sheath is placed into such a patient.

The "axial direction" of an elongate component refers to a direction along the center axis of the elongated component.

FIG. 1 is a top view of a first embodiment of the present invention which is an introducer sheath 10 that has a tubular shaft 11 and a hemostasis valve fitting 12 located at the proximal end of the introducer sheath 10. A hydrophilic lubricious coating could be applied to the either or both the interior and exterior surfaces of the shaft 11. However, it is conceived to not extend the lubricious surface to where it passes through the patient's skin. The darkened region 11A in FIG. 1 could be the only surface of the shaft 11 that is not covered with a lubricious coating. For example, the lubricious exterior coating might extend only to within approximately 1.0 to 2 cm. from the surface of the hemostasis valve 12 and optimally the length of the region without a lubricious coating would be less than 5.0 cm. In that way, there is some increase in the tendency of the shaft 11 to be retained in the position where it is placed through the skin.

A side arm 14 of the introducer sheath 10 would have a cylindrical tube 15 which has a two-way stop cock 16 located at the proximal end of the tube 15. The valve handle 19 of the stop cock 16 can be used to select between either one of the two Luer fittings 17 or it can close off the distal end of the side arm 14. The side arm 14 is used to flush out the introducer sheath 10 before its placement into a blood vessel of a human subject and to inject medications after an interventional procedure is completed. The stop cock 16 can be closed so as to disallow any leakage of blood through the side arm 14 after the introducer sheath 10 is placed into the patient's vascular system.

Figure 2:
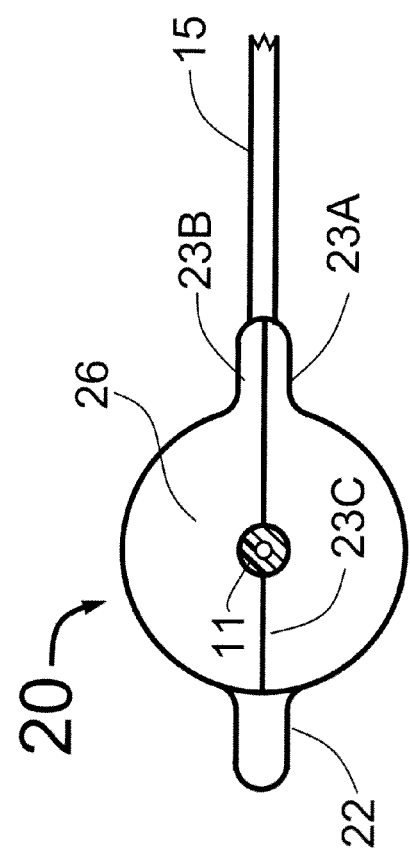
FIG. 2 is an end view of the sheath at Section 2-2 of FIG. 1.

As seen in FIGS. 1 and 2, an adhesive pad 20 is placed around the shaft 11 at the distal end of the strain relief 18. The adhesive pad 20 has a main body 24 onto which is attached a pressure sensitive adhesive 25 (as seen in FIG. 1) that is covered by a removable plastic cover sheet 26 having removal tabs 23A and 23B (as seen in FIG. 2). The plastic sheet 26 is split along the line 23C so that it can be easily removed from each side of the shaft 11. The pressure sensitive adhesive 25 is placed upon the surface of the main body 24 which main body is ideally a spongy material that is covered by a thin plastic cover sheet 21 that is fixedly attached to the spongy material of the main body 24. The tab 22 of the plastic covering 21 is used to remove the adhesive pad 20 from the patient's skin at the conclusion of the medical procedure. By the omission of an adhesive on the tab 22, it is easier for the operator to remove the adhesive pad 20 from the patient's skin at the completion of the procedure when the introducer sheath 10 is to be removed from the patient's body. Although the cover sheet 26 is shown having two pieces in FIG. 1 it could be formed as one piece or 3 or more pieces. It could also be made of regular paper, waxed paper or paper with a plastic coating. Ideally the adhesive pad 20 can be angled with respect to the longitudinal direction defined by the tube 11 so that the adhesive pad 20 can be more easily attached to the skin even if the tube 11 is inserted through the skin at an angle other than 90 degrees.

Another advantage of the design of FIGS. 1 and 2 is that the adhesive will cover the hole in the skin where the shaft 11 of the sheath 10 penetrates the skin. This covering will tend to prevent any bleeding that might otherwise occur at the place where the shaft 11 is placed through the patient's skin.

FIG. 1 also shows a suture tab 13 placed onto the side of the hemostasis valve 12. In some embodiments, the present invention conceives of having this suture tab 13 located at the proximal end of the introducer sheath to be used if for any reason that the adhesive pad 20 fails to adequately adhere to the patient's skin. Specifically, the present invention conceives of the combination of an adhesive pad 20 with a backup of a suture tab 13 in some instances.

Although FIGS. 1 and 2 show the adhesive pad 20 at a location in close proximity to the hemostasis valve 12 and wrapped around the shaft 11, it is also conceived that the adhesive pad be could be placed at other locations at or near the proximal end of the introducer sheath 10. For example, the present invention envisions an adhesive pad placed around the shaft 11 and fixedly attached to the distal surface of the hemostasis valve fitting 12 without any strain relief being used, in some embodiments. Also, FIGS. 3, 4A, 4B, 5 and 6 illustrate alternative embodiments of the present invention each of which has an adhesive pad that is located at the proximal end of the introducer sheath with the adhesive pad attached to the hemostasis valve. It is also conceived that the adhesive layer 25 could be impregnated and elute an antibiotic medication to reduce the probability of infection at the insertion site.

Figure 3:
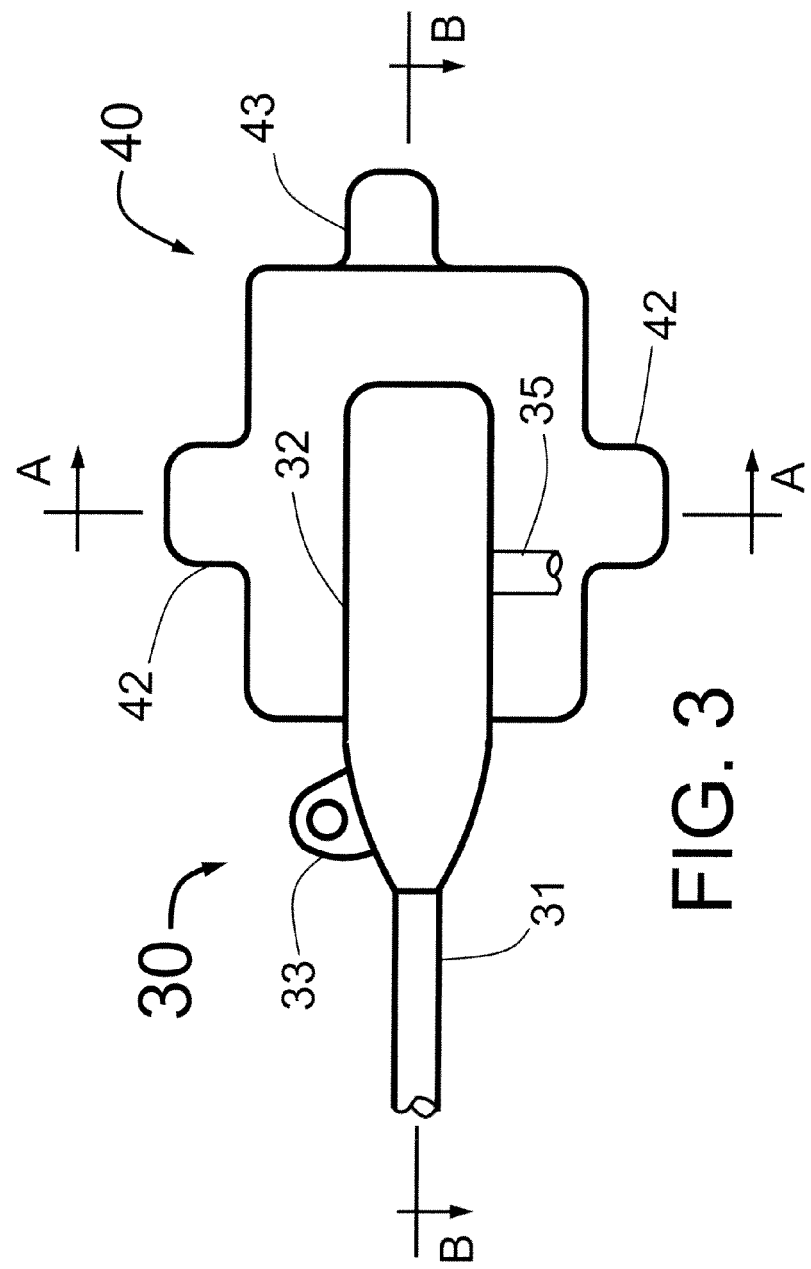
FIG. 3 is a top view of an alternative embodiment of the present invention wherein the adhesive pad is attached to the bottom surface of the hemostasis valve.

FIG. 3 is a top view of an alternative embodiment of the present invention which is an introducer sheath 30 having an adhesive pad 40 attached to the bottom surface of the hemostasis valve 32. FIG. 3 shows a suture tab 33 that can be used with a suture as an alternative means for the operator to attach the proximal end of the introducer sheath 30 to the patient's skin. FIG. 3 also shows that the introducer sheath shaft 31 and side arm 35 are each placed into the hemostasis valve 32 that has a front entrance port 37 (as seen in FIGS. 4A and 4B). As seen in FIG. 4B, within the hemostasis valve 32 is a diaphragm 36 through which a guiding catheter or similar catheter can be placed. The purpose of the diaphragm 36 is to prevent the back backward flow of blood whether or not any catheter is placed through the diaphragm 36. To decrease the force that is required to either advance a guiding catheter through the hemostasis valve diaphragm 36 in a forward direction or pull a guiding catheter back out of the diaphragm 36, such a diaphragm 36 could be treated with a lubricious, typically hydrophilic, coating such as those used on the outer surface of some introducer sheaths. FIGS. 3, 4A and 4B also show that the adhesive pad 40 includes a spongy pad 41, a tab 42 to remove the adhesive pad 40 from the patient's skin after the procedure is completed and a tab 43 that is used to pull a plastic cover sheet 46 off of the pressure sensitive adhesive 45. The use of a comparatively thick and spongy adhesive pad 41 allows the hemostasis valve 32 to be more effectively joined by the pressure sensitive adhesive 45 to a surface of the skin that could be somewhat irregular. The plastic sheet 46 that covers the pressure sensitive adhesive 45 is removed just before the adhesive pad 40 is attached to the patient's skin. It is also conceived that the spongy pad 41 could be impregnated and elute an antibiotic medication to reduce the probability of infection.

Figure 5:
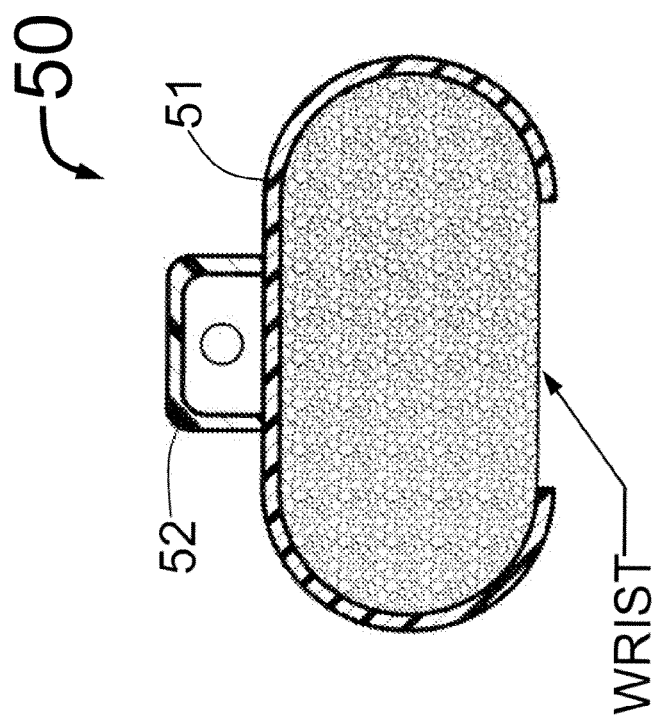
FIG. 5 is a cross section of the wrist at the site of the hemostasis valve with an adhesive wrap connected to the bottom surface of the hemostasis valve, the adhesive wrap being placed around a patient's wrist.

FIG. 5 is a cross section of an introducer sheath 50 showing a hemostasis valve 52 that has an adhesive pad 51 attached to its bottom surface. The adhesive pad 51 could be partially or completely wrapped around the patient's wrist to secure the introducer sheath 50 to the patient's wrist.

Figure 6:
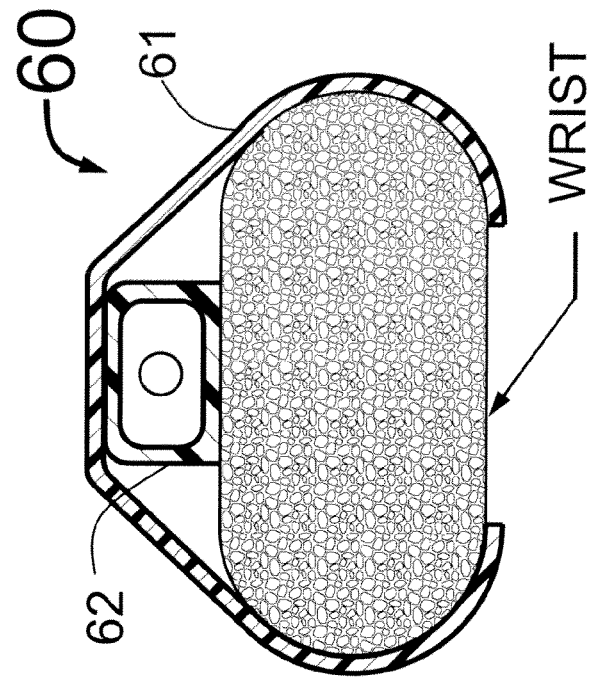
FIG. 6 is a cross section of the wrist at the site of the hemostasis valve with an adhesive wrap connected to the top surface of the hemostasis valve, the adhesive wrap being placed around a patient's wrist.

FIG. 6 is a cross section of an introducer sheath 60 showing a hemostasis valve 62 that has an adhesive pad 61 attached to its top surface. The adhesive pad 61 could be partially or completely wrapped around the patient's wrist to secure the introducer sheath 60 to the patient's wrist.

Figure 7:
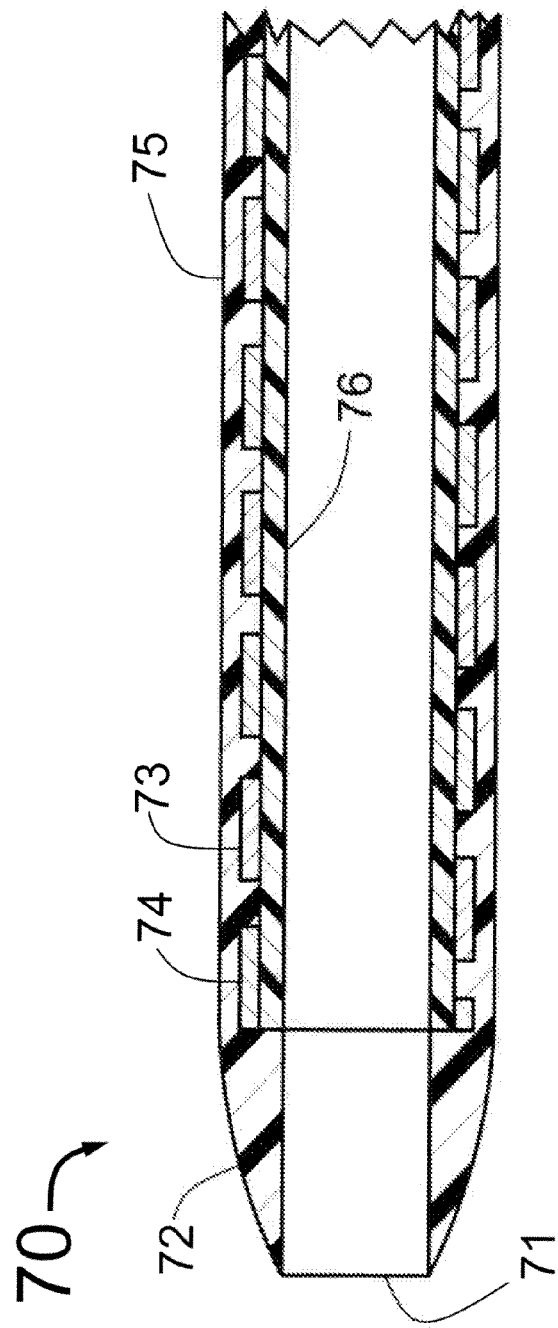
FIG. 7 is a cross section of a distal portion of a thin-walled shaft of an introducer sheath utilizing two helices of different metal alloys each helix having a specific characteristic that is advantageous for the design and functioning of the sheath.

FIG. 7 is another feature of an embodiment of the present invention showing a sheath shaft 70 of a novel, thin-walled design which has a distal opening 71 and a tapered distal end 72. To minimize the opening in the patient's skin, the shaft 70 should be as thin-walled as can be achieved. To have a very thin wall, the shaft 70 could be fabricated from two or more thin-walled, flat-wire, metal helical coils 73 and 74 with plastic material on either or both of its interior and exterior surfaces. The inner plastic layer 76 might typically be made from PTFE or any similar Teflon-like, slippery material. The outer plastic layer 75 could typically be Pebax or any similar polymer. The helical metal coils 73 and 74 would be fabricated from flat wires that would optimally be approximately 1 to 3 mils in thickness and about 10 to 30 mils in width. The space between coils would be between 1 and 30 mils with the optimal spacing being between one tenth and nine tenths of the wire's width. The metal for each of the coils 73 and 74 could be stainless steel, a shape memory alloy or a cobalt chromium alloy (such as L605) or any equivalent metal alloy. A key feature of the shaft 70 is that the flat wires 73 and 74 would be made from different metal alloys. Although FIG. 7 shows two helices of flat wire 73 and 74, it should be understood that as many as four separate flat wires could be used for the shaft 70. Optimally at least one of the flat wires would be stainless steel because that is an inexpensive metal alloy. If radiopacity is desired for the shaft, then at least one of the two to four wires would be made from a very dense metal alloy such as the cobalt-chromium alloy L605. If a shape memory alloy is desired to increase resistance against kinking of the sheath, then the metal alloy Nitinol could be used for at least one of the flat wires for the shaft 70. The Nitinol would be treated to maintain its helical shape at a temperature that is below body temperature and preferably below room temperature. The advantage of Nitinol is that in its superelastic state above the transition temperature, such a shaft 70 would be non-kinking even though it would have a very thin wall. An optimum design to achieve radiopacity with minimum cost would be to have one helical coil fabricated from a cobalt-chromium alloy flat wire and one to three additional coils would be made from stainless steel to minimize the coat of the shaft material. An optimum design to avoid kinking of the shaft would use one helix of Nitinol and a second helix of stainless steel to minimize cost of the shaft material.

By having very thin flat wire coils 73 and 74 and a thickness of plastic on each side of that metal coil that is just a few mils thick, the outside diameter of such a shaft 70 would be very much smaller than the outside diameter of any existing introducer sheath having the same inside diameter. An optimum thickness for the shaft 70 would be less than 7 mils and still better, it would be approximately 5 mils in thickness. It is also conceived that a very small diameter wire with a circular cross section could be used instead of the flat wire to form the helical structure to support the tubular shaft or the introducer sheath. Still further, the flat wire could be formed as a braid which is two flat wire helical coils that are interlaced. The present invention conceives that this thin-walled wire structure with such an extremely small wall thickness constitutes a significant improvement over the prior art. What the present invention claims, in some embodiments, is a new concept of thin-walled introducer sheaths whose outside diameter is at least 1.0 French size smaller than any other introducer sheath of comparable inside diameter and optimally a full 1.5 French size smaller outside diameter. Such a reduction in the outside diameter of the introducer sheath's shaft 70 can significantly reduce bleeding at the patient's groin which bleeding can require that the patient requires a blood transfusion. Thus, the present invention claims a method for decreasing the percentage of patients who require a blood transfusion after an introducer sheath has been used to access the patient's vascular system, in some embodiments. This method includes forming of a thin-walled, flat-wire, helical coil within the sheath with the helical coils made from two different metal alloys onto which a plastic material is placed onto each side of these helical coils. The method also includes the step of forming the wall thickness of a tubular shaft 70 to be less than 7 mils and as small as 5 mils. The final aspect of this method is to use such a thin-walled tubular shaft as part of an introducer sheath that is used to access a patient's vascular system.

Figure 8:
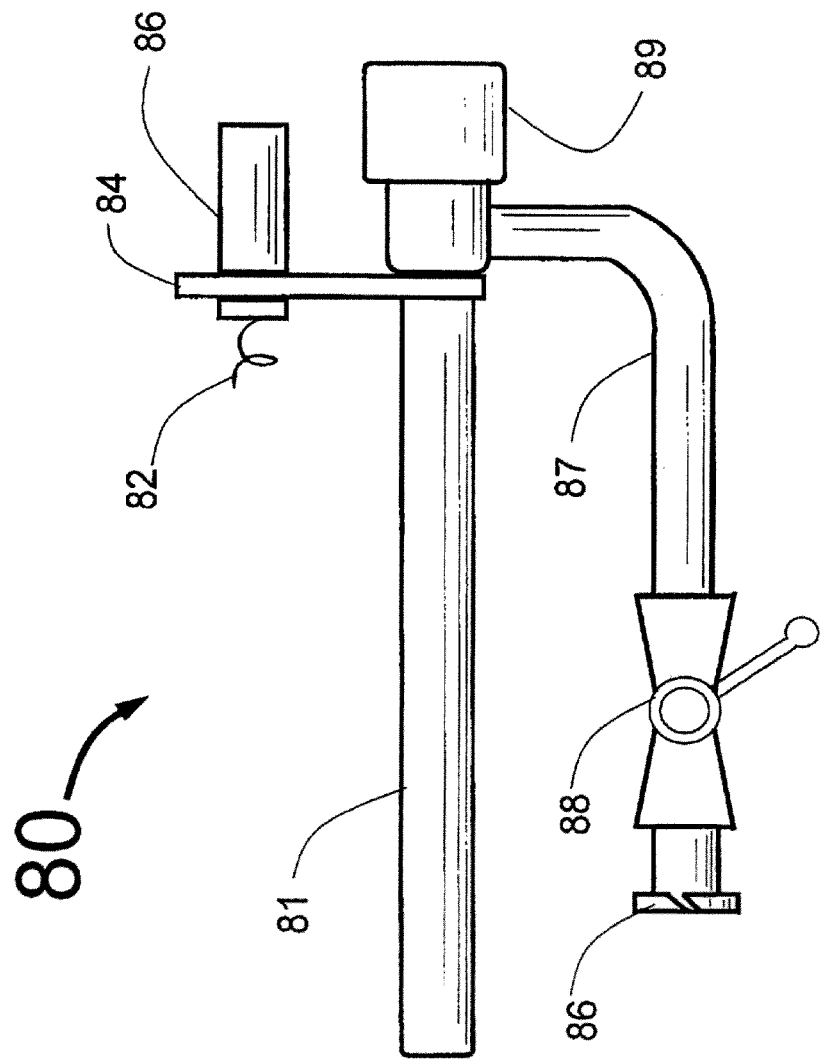
FIG. 8 is a drawing of still another embodiment of the present invention sheath having a corkscrew-like, self-taping wire for affixing the proximal end of the sheath at the insertion site.
Figure 9:
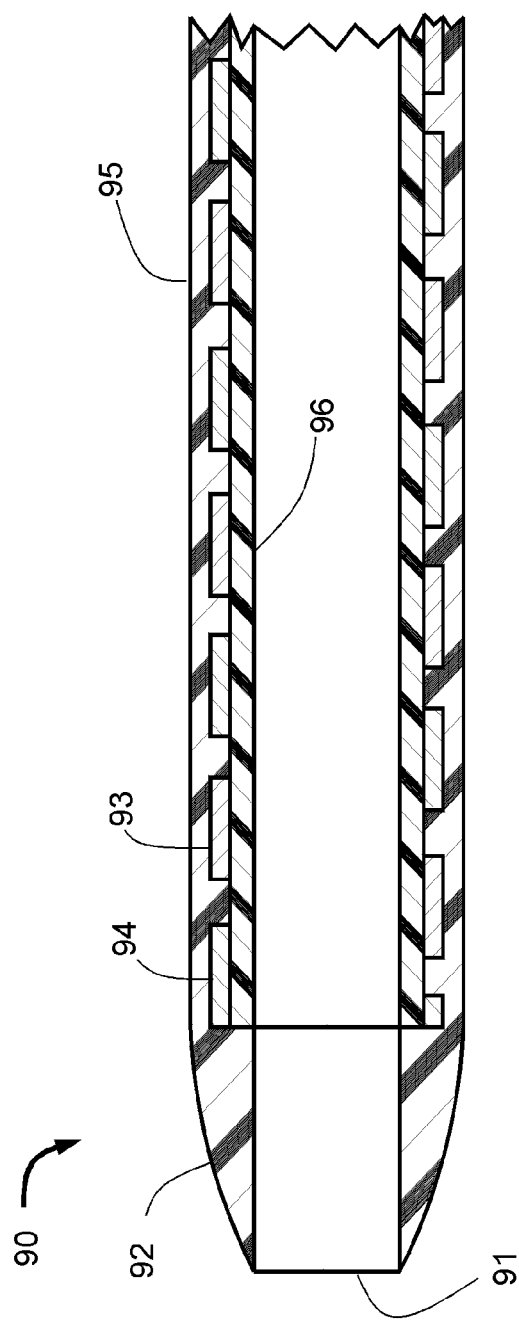
FIG. 9 is a longitudinal cross-section of portions of another embodiment of a thin-walled introducer sheath.

FIG. 8 is a sketch of still another embodiment of the present invention sheath 80 having a corkscrew-like, self-taping wire 82 with handle 86 and connector 84 for affixing the proximal end of the sheath 80 to the skin near the insertion site. The sheath 80 also includes hemostasis valve 89, shaft 81, side arm 87 with valve 88 and Luer attachment port 86. By providing the corkscrew wire 82 and handle 86 which is turned like a corkscrew to screw the wire 82 into the patient's skin, it saves time for the doctor who does not need to apply a separate suture to attach the proximal end of the sheath 70 to the patient's skin. It should be noted that the handle 86 and corkscrew 82 could be rotated by 90 degrees from the position shown in FIG. 8 in order to more readily attach the corkscrew 82 to the patient's skin. It is also envisioned that to save time, instead of a corkscrew wire 82 and handle 86, the integrated attachment means could be a needle and suture cord that could be attached to the hemostasis valve so as to not require a separate suture FIG. 9 is a longitudinal cross-section of portions of one embodiment of a thin-walled introducer sheath. In the embodiment of FIG. 9, the sheath includes an elongated, hollow shaft 90 with a distal opening 91 located at the distal end of the shaft 90. In the illustrated embodiment, the shaft further includes an inner coating 96, an outer coating 95, and one or more scaffolding coils 93, 94 are disposed between the inner 96 and outer 95 coatings. In other embodiments, the scaffolding coils 93, 94 may only be coated on the inside or on the outside diameter of the coils.

The inner coating 96, the outer coating 95, and the scaffolding coils 93, 94 may be configured such that the total wall thickness of the shaft 90 is minimized. In some embodiments, the scaffolding coils 93 are configured to provide strength, provide enhanced radiopacity, and to resist kinking and other deformation. In the illustrated embodiment, the outer coating 95 is further configured to seal the structure and to confine the coils 93, 94 to prevent them from unwinding or losing their shapes.

In some embodiments, the inner coating 96 is formed of a polymer such as polytetrafluoroethylene (PTFE), for example. In other embodiments, other plastics, including plastics with relatively low coefficients of friction, may also be used. In some embodiments the inner coating 96 is configured as a low friction coating, facilitating the passage of elongated instruments through the shaft 90.

In some embodiments, one or more helical coils 93, 94 are coupled to the inner coating 96. In the embodiment of FIG. 9, for example, two separate helical coils 93, 94 are illustrated. In other embodiments, a sheath may include only a single helical coil or include multiple helical coils, such as, for example, two, three, or four total helical coils. In some embodiments, for example, the embodiment of FIG. 9, each helical coil is composed of a single helically wound coil of wire.

Though the helical coils 93, 94 described in connection with FIG. 9 are referred to above as "coils" or "helical coils," any shape, configuration, or type of scaffolding structure is within the scope of this disclosure. Similarly, though the helical coils 93, 94 are referred to above as "wire" structures, it is within the scope of this disclosure to form these scaffolding structures from any material, including metals, polymers, and fibers, including organic and inorganic fibers. Similarly, regardless of the material used, the "wires" or strands of material within the scope of this disclosure may be flat, or may have a cross-sectional profile which is substantially circular, elliptical, rectangular, square, or multisided.

In some embodiments, the helical coils 93, 94 are metal wires wound in helical shapes about the inner coating 96. The distance between adjacent coils on each helix is from about 0.001 inch to about 0.100 inch, in some embodiments.

Certain embodiments within the scope of this disclosure include more than one helically wound wire; in some such instances the helices intersect, while in others they are substantially parallel. For example, in some instances two helical wires could be interlaced, or wound in opposite directions, forming a braided wire structure around the diameter of an introducer sheath.

In the embodiment of FIG. 9, the coils 93, 94 are formed of flat wires wound in helical shapes which do not intersect. In differing embodiments, the wires are from about 0.001 inch to about 0.005 inch thick, including from about 0.001 inch to about 0.004 inch thick or from about 0.001 inch to about 0.003 inch thick. Furthermore, depending on the embodiment, the coils 93, 94 are from about 0.005 inch to about 0.030 inch in width.

In the embodiment of FIG. 9, the shaft 90 includes two helical coils 93, 94 which are substantially evenly spaced along the length of the helices. In certain embodiments, the distance between the two helically wound wires 93, 94 is from about one 0.0005 inch to about 0.060 inch. In some embodiments the distance between helices is proportional to the width of the wires, including embodiments where the distance is from about one-tenth to about twice the width of the wires.

In some embodiments, the flat wire helices 93, 94 are formed of metal wires, including embodiments where the wires 93, 94 are stainless steel, a shape memory alloy such as Nitinol, and/or a highly radiopaque metal alloy such as a cobalt chromium alloy such as the alloy L605.

The embodiment of FIG. 9 includes a first helical coil 93 which, in some embodiments, is formed of a relatively inexpensive material such as stainless steel and a second helical coil 94 which, in some embodiments, is formed from a radiopaque material such as a cobalt chromium alloy. In another exemplary embodiment, a shaft 90 includes four total coils, three formed of stainless steel and one formed of a cobalt chromium alloy. Such a combination of materials may be utilized to create an introducer sheath shaft with desired properties of stiffness, resiliency, and radiopacity while also minimizing the material cost of the introducer sheath.

In other embodiments one or more coils are formed of a shape memory alloy such as Nitinol. Use of a shape memory alloy is configured to increase resistance to kinking in some embodiments. In some instances, the Nitinol is treated to maintain its shape, for example, a helical shape, at temperatures below body temperature and/or below room temperature. Nitinol or other shape memory alloys may be used to reduce the incidence of kinking, due at least in part to the superelastic state of shape memory alloys above their transition temperatures. Furthermore, one or more Nitinol wires may be used in conjunction with one or more stainless steel wires to create a sheath with desired properties while minimizing cost.

In the embodiment of FIG. 9, the wire scaffolding structures 93, 94 are coated with an outer coating 95. In the illustrated embodiment, the outer coating 95 forms the outside structure of the shaft 90 of an introducer sheath. In some embodiments the outer coating 95 is formed of a polymer, such as Pebax, for example. The outer coating 95 forms the outer structure of the shaft 90 as well as functions to confine the coils 93, 94 in some embodiments. For example, the outer coating 95 may be configured to prevent scaffolding structures comprising helical coils from expanding, unwinding, or otherwise undesirably deforming.

In some instances, metal wires may have significant residual stresses introduced when the wire was formed. For example, some metal wires are formed by drawing, or pulling the wire through a die. Drawing wires can introduce internal stresses as the material is cold worked. Cold worked wires can be hard, brittle, or tend to unravel once formed into a helical shape. Thus, in some embodiments, cold worked wires require a thicker outer coating 95 to contain the coil, once the coil is incorporated into a sheath. Accordingly, in some embodiments, the wire coils 93, 94 are heat treated to a substantially soft condition so as to reduce hardness and residual stresses that result from cold working the material. In one exemplary embodiment, metal wires are annealed before being shaped into helical coils having the desired coil spacing and diameter. Use of annealed coils decreases the required thickness of the outer coating 95 in some embodiments, because annealing can decrease forces which would tend to unwind the coil or force the coil outward so as to deform the outer coating 95.

As used herein, references to "annealing" are to be interpreted broadly. Annealing thus refers to any heat treating process (including processes comprising heating and cooling the material) configured to remove internal stresses and/or make the material less brittle. As used herein, the term does not require the metal to be treated at any specific temperature or for any specific amount of time. Further, metal is annealed within the meaning of this definition if the heat treatment is configured to remove any amount of cold-work-related residual stresses or hardness; it is not required that the annealing process remove all such stresses or hardness.

In some embodiments, use of annealed coils 93, 94 is used to reduce the overall diameter of an introducer sheath shaft 90, because the required thickness of the outer coating 95 may be minimized. In some instances, the wall thickness of the shaft 90 are less than 0.010 inch thick, including embodiments where the wall thickness is less than 0.005 inch.

In some instances, use of annealed coils, in connection with the other disclosure provided herein, enables the production of a thin-walled introducer sheath 90 with an outside diameter from about 1.0 or 1.5 French size smaller than an introducer sheath of comparable inside diameter formed by other methods.

In some embodiments, an introducer sheath is formed by first obtaining wire material to be formed into coils. The wire is then annealed to remove residual stresses introduced when the wire was formed. The annealed wire is then formed into the desired shape, for example helical coils 93, 94. In some instances the wire is so formed by wrapping the wire only onto the inner coating 96. For example, a single, flat wire may be wound in a single layer onto an inner coating 96 formed of a lubricous polymer. Additionally, in some embodiments, one or more additional wires are subsequently wound onto the inner coating 96. Continuing with the prior example, once the first flat wire is wound onto the inner coating 96, a second flat wire could be wound onto the inner coating 96. Alternatively, as many as four wires of at least two different metal alloys could be wound onto the inner coating 96 at the same time. In some examples, as many as four separate flat wires are disposed in substantially parallel helices. In such instances, as many as four flat wires are disposed within the same layer of the sheath, and the as many as four wires do not cross or overlap each other. In other examples the helices of two to four wires may be opposed such that the wires form a crossing pattern or weave. Additionally, a fifth, a sixth, or more wires can be added to this exemplary embodiment, including embodiments where none of the wires overlap.

The inner coating 96 and coils 93, 94 are then covered by the outer coating 95.

In some examples, the wires are annealed in a furnace or oven before the wires are formed into coils 93, 94 on the inner coating 96. Thus, in certain embodiments, the entire length of wire is annealed. In some instances the wires are annealed within a furnace while the wire is surrounded by an inert gas, such as nitrogen. Further, in some embodiments where multiple coils of more than one material are incorporated into the sheath, each type of wire is annealed under different conditions, such as at different temperatures and different times for heat treating and cooling. For example, flat wire stainless steel can be annealed by heating the wire to a temperature of about 1,200 degrees Fahrenheit for at least ten minutes, then slowly cooling the wire to room temperature. Additionally, some radiopaque flat wires, such as cobalt chromium, are annealed at temperatures between about 1,400 degrees and about 1,600 degrees Fahrenheit, then slowly cooled to room temperature. In some situations, the wires are annealed in large batches, then smaller portions of the wire are used to form individual introducer sheathes. Whether the wires are annealed in large quantities or after being formed into shorter lengths, use of a furnace or oven to anneal the wires causes the entire length of the wire to be annealed. In some embodiments, the wires are annealed to a soft condition so that they do not push out against the outer coating 95 which could distort that outer coating. Once the wires have been formed onto the inner coating 96, they become work hardened when they are formed into a helix. This work hardening after they have initially been annealed to soften the wires 93, 94 helps to strengthen the wall of the shaft 90.

In the embodiment of FIG. 9, the introducer sheath further includes a tapered distal tip 92 that surrounds the distal opening 91. The tapered distal tip 92 can be shaped by heat forming the outer coating 95 of the introducer sheath. In some embodiments the tapered distal tip 92 is integrally formed with the outer coating 95. The taper facilitates passage of the introducer sheath through the skin or other tissue of a patient in some instances.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein.

The invention claimed is:

1. An introducer sheath including:
an elongated tubular shaft, having a distal end and a proximal end, the shaft comprising:
an inner coating;
an outer coating disposed around an outside diameter of the inner coating; and
a wire layer disposed between the inner coating and the outer coating, wherein the wire layer comprises a first annealed wire helix and a second annealed wire helix, wherein the first annealed wire helix comprises a cobalt-chromium alloy and the second annealed wire helix is made from either stainless steel or Nitinol, wherein the first and second annealed wire helices are wound parallel to one another such that they are non-overlapping.

2. The introducer sheath of claim 1, wherein the first annealed wire helix comprises cobalt chromium alloy L605.

3. The introducer sheath of claim 1, wherein the first annealed wire helix comprises a cobalt chromium alloy and the second annealed wire helix is stainless steel.

4. The introducer sheath of claim 1, wherein the inner coating is polytetrafluoroethylene (PTFE) and the outer coating is Pebax.

5. The introducer sheath of claim 1, further including a third annealed wire helix disposed between the inner coating and the outer coating.

6. The introducer sheath of claim 5, further including a fourth annealed wire helix disposed between the inner coating and the outer coating.

7. The introducer sheath of claim 1, wherein the first and second annealed wire helices each have a flat cross-section.

8. The introducer sheath of claim 1, wherein the first annealed wire helix is radiopaque.

9. The introducer sheath of claim 1, wherein the first and second annealed wire helices are formed from flat wires which are less than or equal to about 0.003 inches thick.

10. The introducer sheath of claim 1, wherein the total wall thickness of the elongated tubular shaft is less than about 0.010 inches thick.

11. The introducer sheath of claim 1, further including a tapered distal tip.

12. The introducer sheath of claim 11, wherein the tapered distal tip is integrally formed with the outer coating.

13. A method of introducing medical instruments into the vasculature of a patient, including:
    obtaining the introducer sheath of claim 1; and
    inserting the introducer sheath through the skin of a patient such that the introducer sheath accesses the patient's vasculature.

14. An introducer sheath for placement into the vascular system of a human subject, the introducer sheath having a tubular shaft that comprises a wire layer disposed between an inner plastic coating and an outer plastic coating, the wire layer comprising a first flat wire metal helix comprising a cobalt-chromium alloy and a second flat wire metal helix that is made from either stainless steel or Nitinol, wherein the first and second flat wire metal helices are wound parallel to one another such that they are non-overlapping, wherein the first and second flat wire metal helices are formed from flat metal wires that have been heat treated to minimize the hardness of the flat metal wires.

15. The introducer sheath of claim 14 where the inner plastic coating is made from PTFE or an equivalent plastic material and the outer plastic coating comprises nylon.

16. The introducer sheath of claim 14 where the distal tip of the introducer sheath is formed from the outer plastic coating of the shaft of the introducer sheath.

17. The introducer sheath of claim 14 where the thickness of the wire layer is less than or equal to approximately 3 mils and the wall thickness of the tubular shaft is less than approximately 7 mils.

18. The introducer sheath of claim 14 where the first flat wire metal helix comprises a cobalt-chromium alloy that is radiopaque and the second flat wire metal helix is formed from stainless steel.

19. The introducer sheath of claim 14 wherein the wire layer further comprises a third flat wire metal helix and a fourth flat wire metal helix, wherein the second, third, and fourth flat wire metal helices are formed from stainless steel.

20. The introducer sheath of claim 14 where the first flat wire metal helix comprises cobalt-chromium L605 alloy.

* * * * *